United States Patent [19]

Cadwallader et al.

[11] Patent Number: 4,506,158

[45] Date of Patent: Mar. 19, 1985

[54] DUAL MODE SPECTROMETER TEST STATION

[75] Inventors: Robert H. Cadwallader, Poughkeepsie; Harold D. Edmonds, Hopewell Junction; Murlidhar V. Kulkarni, Fishkill, all of N.Y.

[73] Assignee: International Business Machines Corporation, Armonk, N.Y.

[21] Appl. No.: 471,927

[22] Filed: Mar. 3, 1983

[51] Int. Cl.³ ............................................... G01J 1/00
[52] U.S. Cl. ..................................... 250/338; 356/244
[58] Field of Search ............... 250/338, 339, 341, 347, 250/353, 349, 358.1, 359.1; 356/73, 244, 382

[56] References Cited

U.S. PATENT DOCUMENTS 3,994,586  11/1976  Sharkins ............................. 250/341
3,999,866  12/1976  Mathisen ............................ 356/244

OTHER PUBLICATIONS

Briska et al., "Apparatus and Method for Determining the Carbon Content in Silicon Wafers", IBM Technical Disclosure Bulletin, vol. 23, No. 1, Jun.–1980, p. 225.
Guggenheim et al., "Wafer Transport for IR Analysis", IBM Technical Disclosure Bulletin, vol. 22, No. 2, Jul.–1979, p. 586.

Primary Examiner—Alfred E. Smith
Assistant Examiner—Richard Hanig
Attorney, Agent, or Firm—James E. Murray

[57] ABSTRACT

A new spectrometer station for semiconductor wafers is provided that permits operation in both the reflective and absorption modes either simultaneously or sequentially while the wafer is in a horizontal position. The wafer is positioned in the station on a movable platform. Positioned under the platform is an infrared detector. An optical system over the platform focuses an interferometer beam at that portion of the wafer positioned right over the detector. It also directs light from the beam reflected off the top surface of the wafer at a second infrared detector. An orientor rotates the wafer on the platform so that movement of the wafer by the orientor and movement of the platform allows any part of the wafer to be examined as a test point by the spectrometer.

6 Claims, 10 Drawing Figures

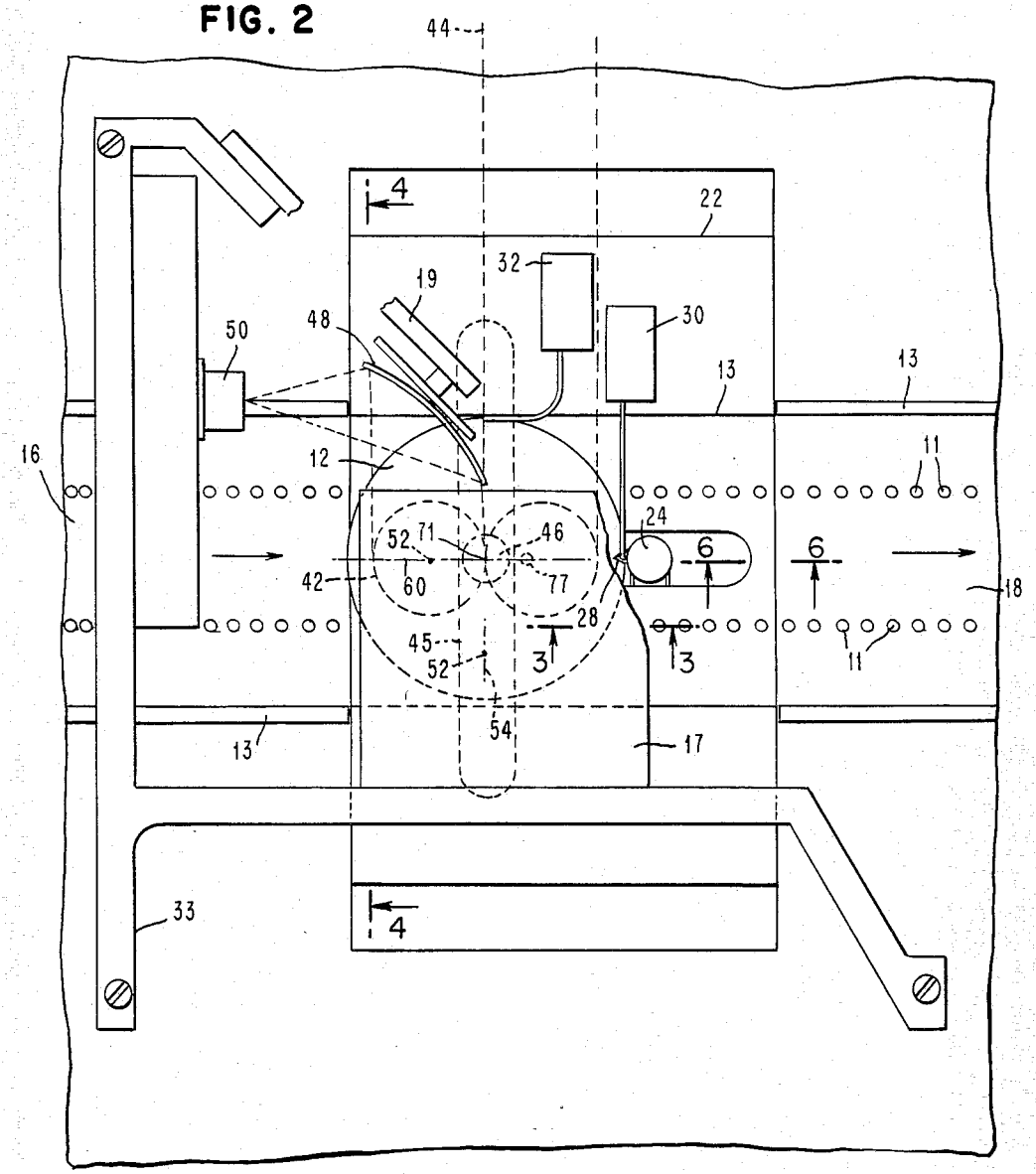

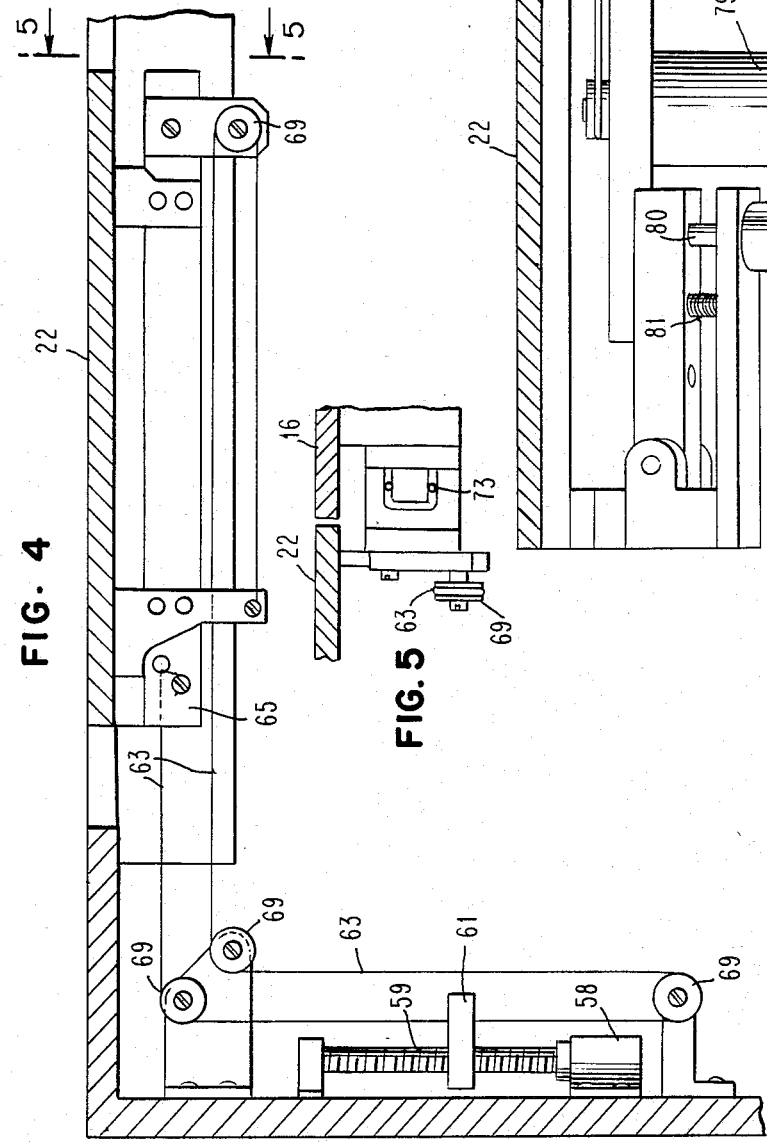

DUAL MODE SPECTROMETER TEST STATION

The present invention relates to spectrometers and more particularly to a testing station that permits the generation of test data on both reflection and absorption characteristics of a test sample.

Spectrographic test data can be obtained by both measuring light reflected from the surface of the test object and also by measuring light transmitted through the test object. For instance, various material parameters of silicon wafers are measured using spectrometers in both modes of data collection. The thickness of epitaxial layers and the carbon and oxygen content of production samples of the wafers are measured to control yields. Fourier transform infrared (FTIR) spectrometers can measure these parameters with speed, accuracy and precision. The carbon and oxygen measurements are made in the absorption mode while epitaxial thickness measurements are made in the reflective mode.

Most conventional wafer systems deliver wafers at a process station in a horizontal position while carbon and oxygen tests have generally been performed on a vertically presented wafer. Therefore, while reflective mode measurements have been performed automatically with such conventional wafer systems measurement of carbon and oxygen content has not.

THE INVENTION

In accordance with the present invention a new spectrometer station is provided that permits operation in both the reflective and absorption modes either simultaneously or sequentially while the wafer is in a horizontal position. The wafer is positioned in the station on a movable platform. Positioned under the platform is an infrared detector. An optical system over the platform focuses an interferometer beam at that portion of the wafer positioned right over the detector. It also directs light from the beam reflected off the top surface of the wafer at a second infrared detector. An orientor rotates the wafer on the platform so that movement of the wafer by the orientor and movement of the platform allows any part of the wafer to be examined as a test point by the spectrometer.

Therefore, it is an object of the present invention to provide a new spectrometer.

It is another object of the invention to provide a new spectrometer test station capable of multimode operation.

It is a further object of the invention to provide a new spectrometer test station which can run tests simultaneously and/or sequentially in reflective or absorptive modes of operation.

THE DRAWINGS

These and other objects of the invention can best be understood by references to the accompanying drawings of which:

FIG. 2 is a top view of the spectrographic test station in FIG. 1 showing an orientor for rotating the wafer in the station;

Figure 7:
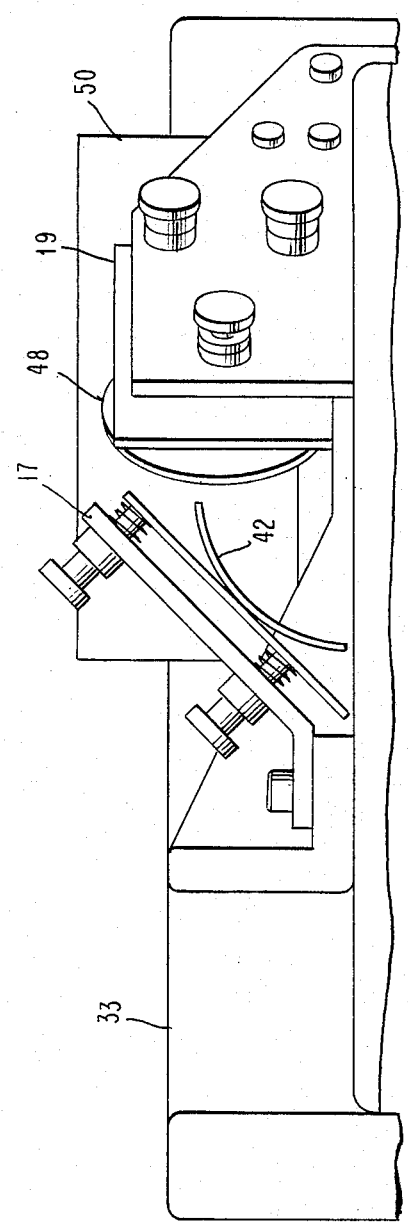
Figure 9:
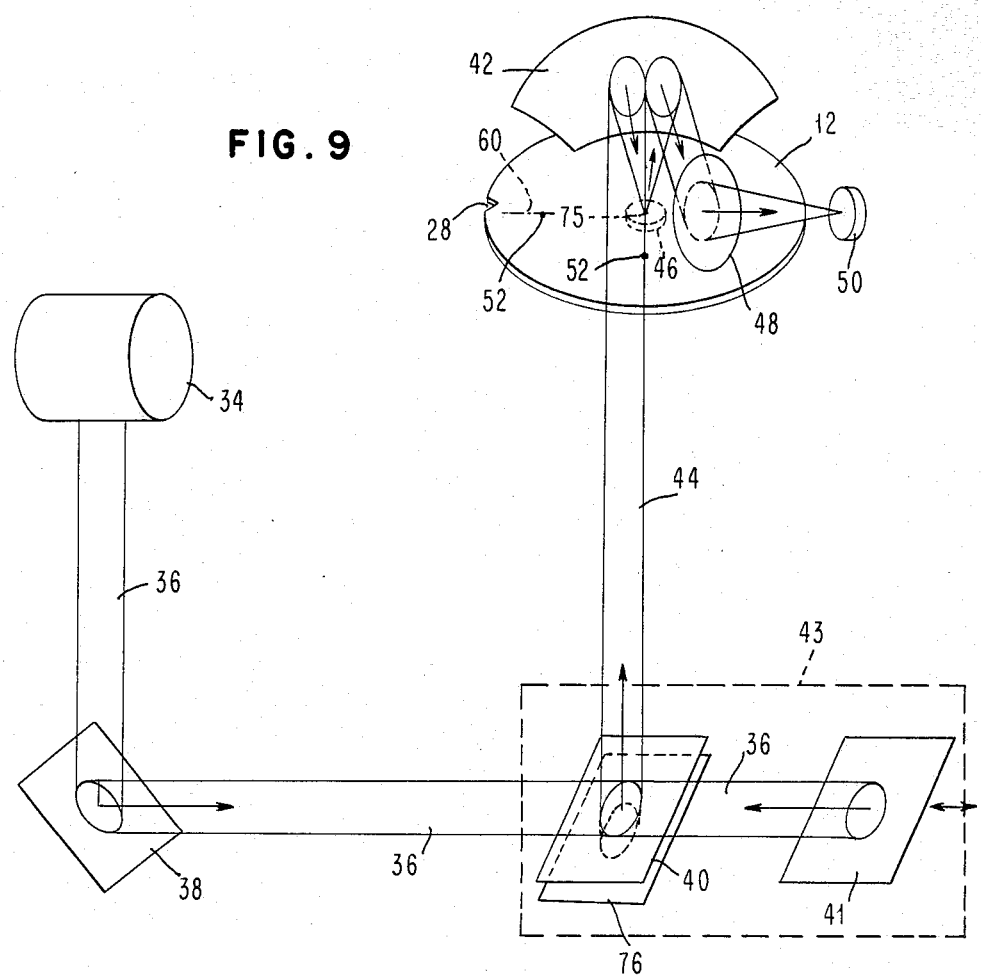
Figure 10:
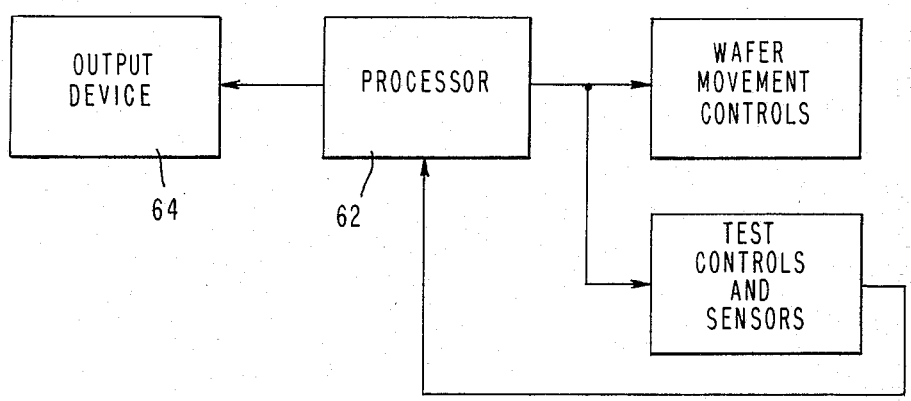

FIG. 3 is a section taken along line 3—3 in FIG. 2;
FIG. 4 is a section taken along line 4—4 in FIG. 2;
FIG. 5 is a section taken along line 5—5 in FIG. 4;
FIG. 6 is a section taken along line 6—6 in FIG. 2;
FIG. 7 is a partial side view of the superstructure in the test station;
FIG. 8 is a schematic representation of drive wheel for the wafer orientor in the test station of FIG. 1;
FIG. 9 is a schematic representation of the optical system in the spectrographic test station of FIG. 1; and
FIG. 10 is a flow diagram for a computer controlled spectrographic test system.

Figure 1:
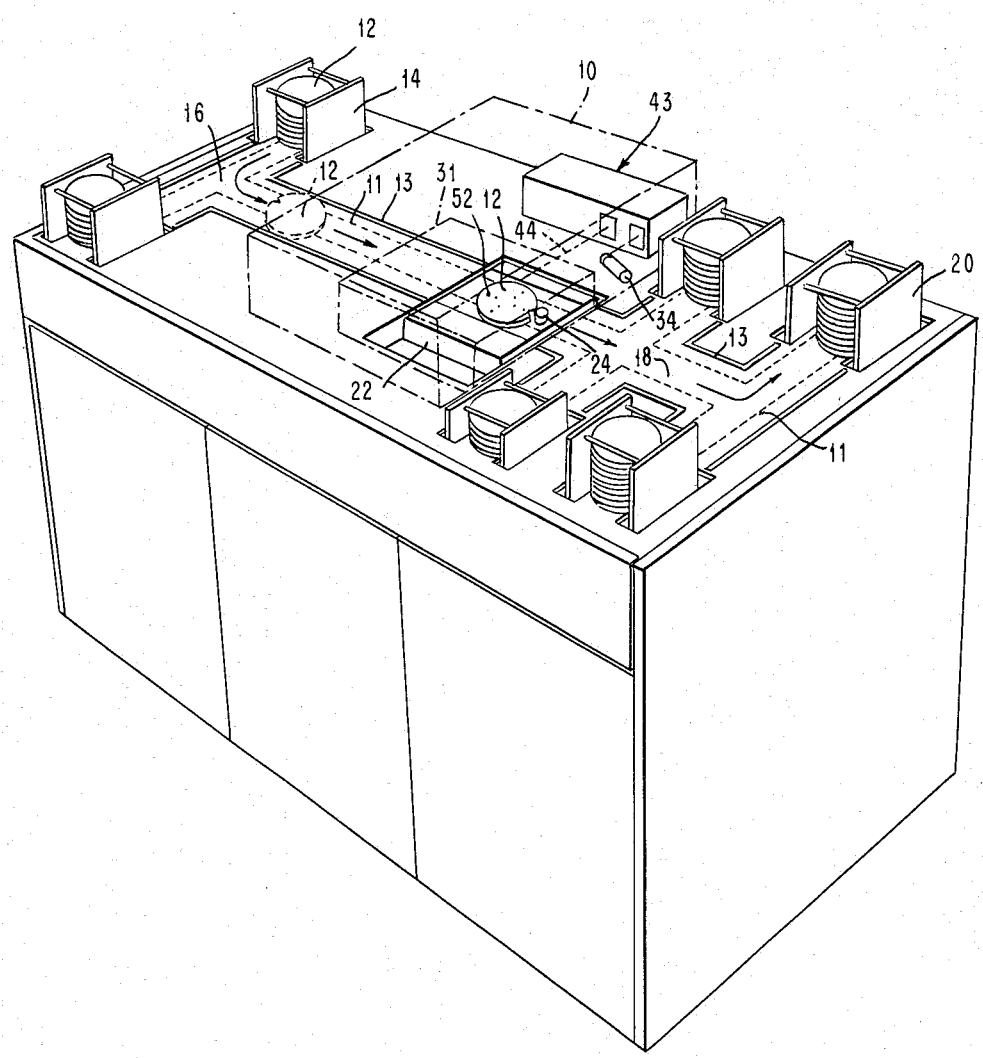
FIG. 1 is a 3-dimensional view of a wafer transport system with a spectrographic test station incorporating the present invention.

Referring to FIG. 1, the infrared spectrometer station 10 is incorporated into an available wafer transport system such as one manufactured by GCA Corp. of 209 Burlington Rd., Bedford Mass. 01730 and described in their manual entitled "Wafer Trac Systems Manual". Wafers 12 loaded into hoppers 14 at one end of this transport system are transported one at a time on an air track 16 into the test station 10. After completion of the test they are transported out of the station 10 on air track 18 into one of the hoppers 20. Loading into one of the hoppers 20 can be done selectively or non-selectively. The wafer 12 can be placed in one or the other of the hoppers 20 on the basis of test results, in some sequential order, or at random.

While a wafer is in the station 10 it rests on a platform or carriage 22 that can move at right angles to the direction of motion of the wafer down the air track 16. As shown in FIGS. 1 to 3, the air track sections 16 and 18 and the platform 2 are provided ports 11 through which air or gas 15 under pressure reaches the top surface of the track 16 and 18 and platform 22 to propel the wafer 12 in the direction of the arrows. Guide rails 13 maintain the wafer on the track and platform. When a wafer 12 enters the station it is driven against a resilient drive wheel 24 and held in contact with the drive wheel 24 by this directional air 15. Contact with the drive wheel 24 causes the wafer 12 to rotate. As the wafer rotates it passes under two electro optic sensors 30 and 32. These sensors 30 and 32 sense the presence of the wafer 12 by light reflection from its surface. Rotation of the wafer 12 with the drive wheel continues until a notch 28 in the edge of the wafer 12 passes under the sensor 30. When this happens, the sensor 30 detects the change in reflected light and activates pneumatics (not shown) which stops the flow of gas 15 and applies vacuum through the port 77 to clamp the wafer 12 to the platform 22. Clamping of the wafer to the top surface of the platform 22, draws the wafer down and away from the canted edge of the drive wheel 24 so that the wafers rotation stops with the notch 28 pointed at the wheel 24.

With the wafer 12 between the guide rails 13 and the notch 28 facing the drive wheel 24, the wafer is located under an optical system 33 which focuses light from an interferometer beam 44 onto the center of the wafer and into an infrared detectors 46 and 50. The two mirrors 42 and 48 and one infrared detector 50 are suspended over the track 16 and carriage 22 on a superstructure 33 which permits unobstructed transport of the wafer on the track 16 and 18 and the carriage 22. The mirrors 42 and 48 are fixed to adjustable mounts 17 and 19 for aligning and focusing the beam at the wafer 12 and two infrared detectors 46 and 50.

As shown best in FIG. 9, a silicon carbide lamp 34 manufactured by Bruker Analytical Messtechnic Wikinger Strasse 13, D-7500 Karlsruhe 21 West Germany, provides an infrared colimated beam 36 which is reflected off mirror 38 into beam splitter 40. Half the energy in the beam 36 is transmitted to mirror 76 and the other half is transmitted into movable mirror 41. The movable mirror 41 oscillates back and forth along the beam's axis at a selected frequency. The light reflected off the movable mirror 41 is directed back onto mirror 40 and deflected with the other half of the beam 38 towards the parabolic mirror 42 to form the interferometer beam 44.

The movable mirror 41 and the half mirror 40 are part of an interferometer 43 such as one of the IR/85 series of FTIR spectrometers available from IBM Instruments, Inc. The interferometer beam 44 is deflected off the parabolic mirror 42 and focused by the parabolic mirror 42 onto the center of the wafer 12. Underneath the wafer is an infrared detector 46 for detecting radiant energy from the interferometer beam 44 that passes through the wafer 12. As shown in FIG. 2, this detector 46 is positioned within a slot 45 in the carriage 22 which has its long axis aligned with the direction of movement of the carriage.

Referring back to FIG. 9, radiant energy reflected off the wafer hits the parabolic mirror at a second point where it is deflected into a concave focusing mirror 48 that focuses it onto a second infrared detector 50. Thus, it can be seen that simultaneous readings can be taken in the reflective and absorptive mode at the center of the wafer.

Tests can be taken on any number of test points 52 along the diameter 54 by movement of the carriage 22 by drive motor 56. As shown in FIG. 4, the motor 58 drives the lead screw 59. The lead screw moves a nut 61. Attached to the nut is a cable 63 that passes over rollers 69 and is attached at both ends to the undercarriage 65 of the platform. As shown in FIGS. 5 and 6, the platform slides on metal bearings 73 on one side of the platform 22 and is supported by an air bearing 75 on the other side of the platform. As the motor 58 drives the lead screw 59, the carriage 22 follows the movement of the nut 61.

Referring back to FIG. 2, when the carriage moves it places different points 52 along the diameter 54 of the wafer 12 at the focus point 71 of the interferometer beam 44. Since the mirrors 42 and detectors 48 do not move the test conditions are the same for all test points 52 along the diameter. The slot 45 in the carriage 22 assures that the detectors view of the wafer 12 is not obscured at any of the test points 52 by the structure of the carriage.

Tests can also be taken along a second diameter 60 which is at right angles to the first axis. After testing is completed along the first axis, the air jets are activated again forcing the wafer 12 against the drive wheel. Sensor 32 is now energized so that it can sense reflection of light off the surface of the wafer 12. The wafer 12 is turned by the drive wheel 24 until the notch 28 is positioned under sensor 32. With the notch under sensor 32 the sensor detects a difference in reflected light and in response thereto pneumatic controls turn off the gas to the ports 11 and applies vacuum through port 77 to clamp the wafer to the platform 22 leaving the wafer 12 on the carriage 22 with the axis 60 aligned with the axis of movement of the carriage. The sampling can now be performed along the axis 60 by movement of the carriage. A case substantially coextensive with the box shown in phantom and marked 10 assures that tests can be made in a non-polluting environment.

After sampling is complete the drive wheel 24 is retracted below the top surface of the carriage 22 and the platform jets are energized to move the wafer 12 off the carriage 22 and onto track 18 where it is transported to one of the hoppers 20.

As shown in FIG. 8, drive wheel 24 is mounted on a pivoting arm 77 along with its drive motor 79. Retraction of the drive wheel below the surface of the carriage is accomplished by energizing a solenoid armature 80 which then pivots the arm downwardly. When the armature is not energized springs 81 maintain the drive wheel 24 in its operational position.

The test station and air track transportation system is part of a spectrographic analysis system. The spectrographic system includes a processor 62 that not only controls the movement on the air track 16 and 18 and in the test station 10 but also runs the tests, receives tests results from the sensors 46 and 50, and analyzes them using suitable FTIR techniques such as those described in articles appearing in the IBM Technical Disclosure Bulletin on pages 1389 and 1390 of the September 1980 issue and pages 49 to 54 of the June 1981 issue. The analysis system supplies the analysis and the test results to an output device 64 for operator examination.

One embodiment of the invention is described obviously a number of modifications and additions of this embodiment are possible without departing from the spirit and scope of the invention as expressed in the claims.

Having thus described our invention, what we claim as new and desire to secure by Letters Patent is:

1. In a spectrographic analysis system for analyzing semiconductor wafers, an automated wafer handling and measurement system comprising:
   first and second wafer storage means for respectively storing a plurality of wafers before and after measurement, said first and second storage means being spaced apart,
   conveying means for transporting wafers serially along a path extending from said first storage means to said second storage means, said path including a measurement station;
   means for directing measurement radiation on a spot in said measurement station where it will impinge on the wafer and cause some of the radiation to be reflected from the wafer and some of the radiation to pass through the wafer;
   rotation and translation carriage means within said station to both rotate said wafer and translate said wafer at right angles to said path in said station to place a plurality of both radially and circumferentially displaced points on said wafer in said spot;
   means respective to the radiation reflected from the wafer to determine the thickness of an epitaxial layer in the wafer;
   and means responsive to the radiation transmitted through the wafer to determine the carbon and/or oxygen content of the wafer.

2. In an infrared spectrographic analysis system which obtains spectrographic data on semi-conductor wafers and analyzes the data to provide physical information about the wafer, a new spectrographic wafer station for generating data on both the reflective and absorptive characteristics of the wafer comprising:
   optical means for directing infrared measurements radiation at a fixed spot in the station,
   carriage means for movement of said wafer in said station to place a number of radially and angularly spaced locations on the wafer at the test point
   first photosensitive means responsive to radiation transmitted through the wafer and
   second photosensitive means responsive to radiation reflected from the wafer.

3. The wafer station of claim 2 wherein said carriage means includes an elongated hole in said carriage means along a diameter of said wafer that includes said first mentioned spot so that the carriage means can translate relative to that first mentioned spot and the first photosensitive means at that spots, and drive means for driving said carriage means coaxially with said diameter so as to change the position of the wafer radially relative to said first mentioned spot.

4. The wafer station of claim 3 including:

orienting means on said carriage to rotate said wafer relative to said first mentioned spot whereby light can be transmitted through the wafer and the hole in the carriage onto the first photosensitive means with the wafer in a number or orientations and positions relative to said first mentioned spot without the carriage structure interferring with the obtaining of test results.

5. The wafer station of claim 4 wherein said optical means includes a single parabolic mirror for both focusing infrared light at said spot and for receiving the reflection from said spot, and focusing mirror focusing the infrared light reflected from said spot onto a second spot.

6. The wafer station of claim 5 wherein said first photosensitive means is located at said first mentioned spot and said second photosensitive means is located at said second spot.

* * * * *